United States Patent [19]
Prescott, Jr. et al.

[11] 4,213,327
[45] Jul. 22, 1980

[54] FLOW BENCH

[75] Inventors: John F. Prescott, Jr., Danville; William H. Roberts, Indianapolis, both of Ind.

[73] Assignee: General Motors Corporation, Detroit, Mich.

[21] Appl. No.: 2,754

[22] Filed: Jan. 11, 1979

[51] Int. Cl.² ............................................. G01M 3/02
[52] U.S. Cl. ............................................................. 73/38
[58] Field of Search ........................................ 73/38, 37.7

[56] References Cited

U.S. PATENT DOCUMENTS

| | | | |
|---|---|---|---|
| 2,993,368 | 7/1961 | Schlein | 73/38 X |
| 3,248,930 | 5/1966 | Speegle et al. | 73/38 |
| 3,371,518 | 3/1968 | Keyes | 73/38 |
| 3,466,925 | 9/1969 | Ziegenhagen et al. | 73/38 |
| 3,590,634 | 7/1971 | Pasternak et al. | 73/38X |

FOREIGN PATENT DOCUMENTS 1063832  8/1959  Fed. Rep. of Germany .............. 73/38

*Primary Examiner*—Gerald Goldberg
*Assistant Examiner*—Joseph W. Roskos
*Attorney, Agent, or Firm*—J. C. Evans

[57] ABSTRACT

A flow bench includes a sealed box with an internal plenum having air flow from a source of pressure directed to several spaced points within the plenum; the sealed box includes an open upper end having a support surface around the open end including undercut spaced parallel grooves at an offset point thereon supporting a pair of seals in sealing engagement with the outer perimeter of a laminated porous panel that completely covers the open end; the flow bench further includes a removable cover. The removable cover includes a peripheral seal plate thereon with an undercut shoulder that accommodates the perimeter of the laminated porous panel and including a groove with a single O-ring therein located above one of the pair of O-ring seals and a plurality of clamp means being provided to bias the seal plate against the outer perimeter of the laminated porous panel to seal the member at the top, bottom and outer surface thereof whereby the air flow through the plenum passes only through the pores of the laminated porous panel thereby to prevent significant sources of error produced by small leakage from other points means are associated with the fluid flow to the plenum to measure the flow rate through the pores of the laminated porous panel to establish an absolute quantitative measurement of flow rate therethrough.

2 Claims, 5 Drawing Figures

FLOW BENCH

The invention herein described is made in the course of work under a contract or subcontract thereunder with the Department of Defense.

This invention relates to apparatus for measuring the rate of coolant air flow through a laminated panel having a plurality of coolant flow pores therethrough and more particularly to apparatus for measurement of flow through such panels when they have a perimeter of substantial extent and with air flow pores extending up to the marginal extent of the full perimeter of the panel being tested.

One type of laminated porous material suitable for use in air cooled turbine engine components is of the type set forth in U.S. Pat. No. 3,584,972, issued June 15, 1971, to Bratkovich et al, for Laminated Porous Metal. In this arrangement thin high temperature alloy metal lamina are diffusion bonded together and are fabricated by photoetching or chemical etching processes to form a plurality of spaced pores in each of the laminates making up the total laminated thickness so as to define an offset air flow path for flow of coolant air through the lamina for cooling the body of metal that surrounds each of the pores in the structure.

In certain applications it is desirable to determine the rate of air flow through such material with quantitative precision at low flow rates. Moreover, it is desirable to determine such air flow rates through panels which are susceptible to buckling throughout the length and width thereof because of the extended dimensions of the test piece.

Various apparatus have been proposed to determine the porosity of a layer of material. Examples of such apparatus are set forth in U.S. Pat. No. 3,371,518, issued Mar. 5, 1968, to Keyes and in U.S. Pat. No. 2,993,368, issued July 25, 1961, to Schlein.

Such apparatus is primarily intended for application in foil type materials and to determine the permeability of the foil to passage of vapor and the like thereacross.

In the device shown in U.S. Pat. No. 3,371,518, the foil material is wrapped around a hollow roll having apertures therein and a generally channel-shaped sealed pressure or vacuum box for producing a pressure differential across foil apertures in a hollow roll. A sheet of foil continuously runs across the roll so that its porosity can be continuously monitored.

The device shown in U.S. Pat. No. 2,993,368 is in the form of a vacuum box having a plurality of anvils on its top against which the material to be tested is placed; when vacuum is applied to the box the material is drawn down against a solid cover having a small number of perforations therein and the amount of leakage into the box is then determined to test whether or not the material is impermeable to gas leakage therethrough.

While the aforesaid devices are suitable for their intended purpose, they are not configured to accept laminated plates of the type set forth in the Bratkovich et al patent.

Accordingly, an object of the present invention is to provide an improved flow bench upon which laminated porous metal of the type used in air cooled gas turbine engine components can be tested for precise quantitative flow rate characteristics and including means for positively sealing a perforated marginal extent of the laminated porous metal to prevent small leaks during air flow across the laminated metal which would otherwise represent a significant source of error in determination of absolute quantitative measurement of low flow rates of air flow through the laminated porous metal.

Still another object of the present invention is to provide an improved flow bench for measuring quantitatively accurate low flow rates through an extended area panel of porous laminated metal by the provision of a sealed air supply box having an internal cavity therein supplied by a source of air through spaced points in the box and including means therein for uniformly distributing air flow through an upward facing opening in the sealed box; the sealed box further including a seal surface thereon including means for properly locating the perimeter of a laminated porous panel thereon and including means for sealing a perforated outer edge of the sheet throughout its perimeter to prevent small leaks at the margin thereof as low flow rates through the porous panel are being measured.

Still another object of the present invention is to provide an improved flow bench for determining the rate of coolant flow through a laminated porous panel by the provision of a sealed box having means for supplying air flow thereto at a very low flow rate for uniform flow through an upwardly facing open end of the sealed box and including a seal surface around the perimeter of the opening for supportingly receiving a perforated perimeter of the porous panel to be flow rated; and wherein a removable seal plate is located in surrounding relationship to the panel for holding it on the support surface including means for maintaining a uniform pressure throughout the perimeter of the porous panel at the outer surface thereof and a seal plate including means associated therewith to supportingly engage the outer surface of the test panel for preventing bowing or buckling thereacross when a pressure differential is applied thereacross thereby to maintain the edges in a uniform plane so as to maintain seal integrity.

Further objects and advantages of the present invention will be apparent from the following description, reference being had to the accompanying drawings wherein a preferred embodiment of the present invention is clearly shown.

Figure 1:
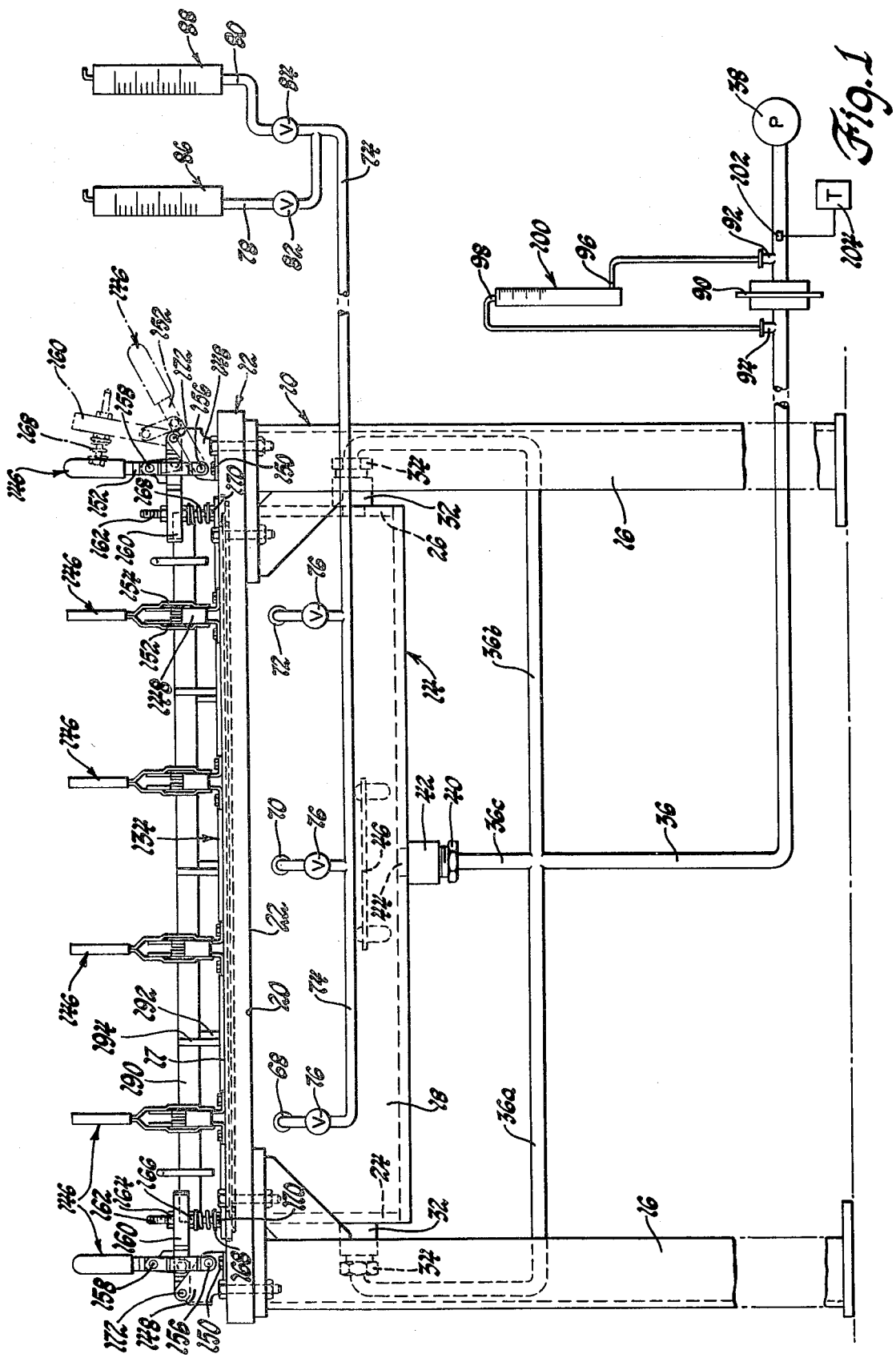
FIG. 1 is a side elevational view of the flow bench of the present invention associated with a pressure source and a pressure sensing system.

Referring now to the drawings, in FIG. 1 a flow bench 10 has an open ended top 12 connected to a sealed air supply box 14. The top 12 has a support column 16 at each corner thereof to locate an upper work surface 17 of the flow bench 10 at a convenient work height.

Figure 3:
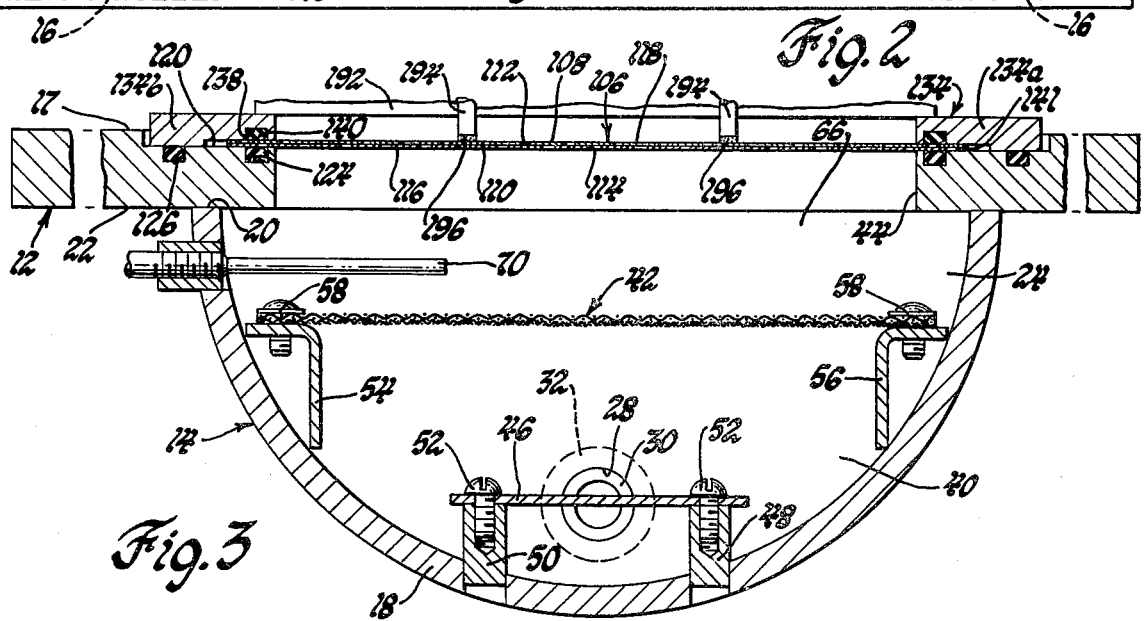
FIG. 3 is an enlarged cross-sectional view taken along the line 3—3 of FIG. 2 looking in the direction of the arrows.

Referring now to FIG. 3, the sealed air supply box 14 includes a generally semicircular cross-sectioned wall 18 with its upper edge 20 located in engagement with the underside 22 of the top 12. The opposite ends of the wall 18 are closed by end plates 24, 26 each of which has an opening 28 therein for supportingly receiving tubular extension 30 of a fluid fitting 32 that is connected by a coupling 34 to opposed branches 36a, 36b of a supply conduit 36 that is in communication with a pressure source 38. The supply conduit 36 further communicates with a branch 36c that is connected by coupling 40 to a fluid fitting 42 having a tubular extension 44 thereon that is supportingly and sealingly received within a segment of the wall 18 at a point equidistant between the end plates 24, 26.

Each of the spaced fittings 32, 42 directs the pressurized fluid for the flow bench 10 into a plenum space 40 that is located below a dual mesh screen 42 that has a planar extent underlying the full planar extent of a generally rectangular top opening 44 in the top 12 of the flow box. Additionally, a baffle plate 46 is located at the bottom of the plenum 40 in overlying relationship to the bottom inlet fitting 42, supported in spaced relationship thereto by a pair of spaced brackets 48, 50 to which the plate 46 is secured by suitable fastening means illustrated as screws 52. Likewise, the dual mesh screen 42 is secured to a pair of support brackets 54, 56 by suitable fastening means representatively shown as screws 58. Thus, fluid flow into the plenum space 40 in uniformly distributed to form a uniform pressure in a pressurizable space 66 in the sealed box 14 at a point immediately underlying the full planar extent of the top opening 44.

Figure 2:
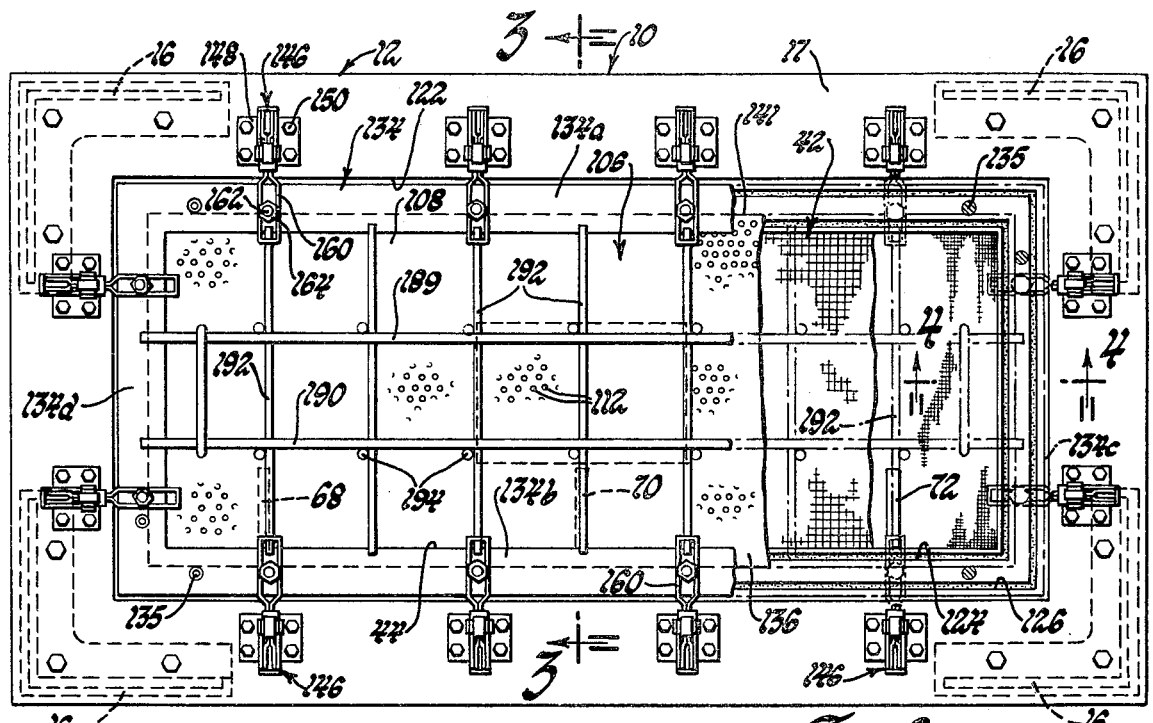
FIG. 2 is a top elevational view of the apparatus shown in FIG. 1.

In the illustrated arrangement, a plurality of spaced pressure probes 68, 70 and 72 are supported on one side of the wall 18 as best shown in FIGS. 2 and 3 for producing an averaged measurement of the pressure within the space 66. Each of the probes 68, 70, 72 is connected to a conduit 74 by valve 76 to flow through branch lines 78, 80 having valves 82, 84 therein to direct the pressure signal to either a water or a mercury manometer 86, 88, respectively.

Additionally, the airflow from the pressure source 38 passes through an orifice plate 90 with a pressure tap 92 upstream and a pressure tap 94 downstream thereof connected to opposite ends 96, 98 of a manometer 100 to indicate the pressure differential across the orifices 90 which when combined with a temperature as sensed by temperature probe 102 and measured by a recorder 104 can be used to accurately determine the rate of flow into the seal box 14 during a test phase of operation to be discussed.

Figures 4, 5:
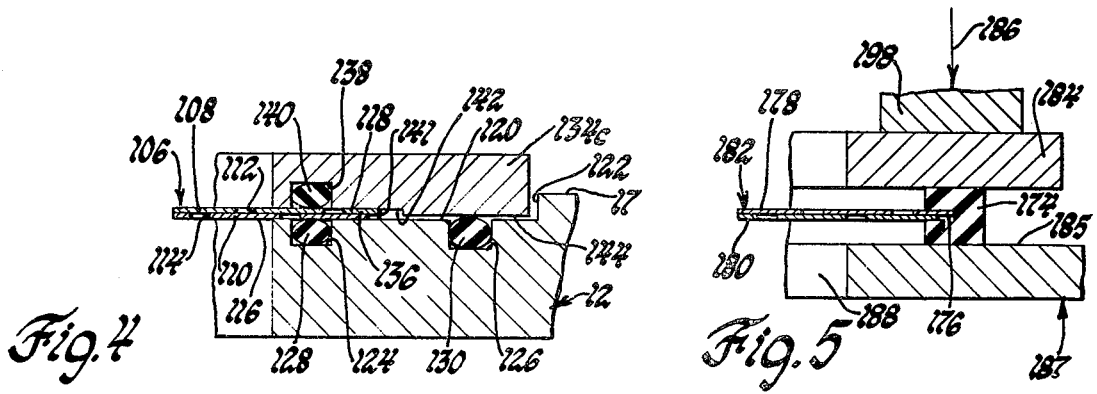
FIG. 4 is an enlarged fragmentary sectional view taken along the line 4—4 of FIG. 2 looking in the direction of the arrows.
FIG. 5 is a view of a fragmentary sectional view like FIG. 4 of another embodiment of the invention.

The pressurization of the space 66 is controlled so that a controlled pressure differential will occur across a test panel 106 that is supported on the top 12 of the flow bench 10. More particularly, in the illustrated arrangement, the test panel 106 is representatively shown as including an outer layer 108 laminated to an inner layer 110 and diffusion bonded thereto. A plurality of pores 112 are formed in the layer 108 and are offset with respect to a like plurality of pores 114 that, together with the pores 112, define a predetermined porosity through the test panel 106 from an inner surface 116 thereon to an outer surface 118 thereof. The periphery of the inner surface 116 is supportingly received on a support surface 120 formed around the perimeter of the opening 44 in the top 12. The support surface 120 is undercut at 122 with respect to the upper work surface 17 of the top 12 as best shown in FIGS. 3 and 4. The support surface 120 includes a first perimetric groove 124 formed therein spaced with respect to a second perimetric groove 126 that extends through both the sides and ends of the surface 120 as best shown in FIGS. 2-4. Resilient O-ring seals 128, 130 are located in the grooves 124, 126 respectively. They cooperate with the underside 132 of a seal plate 134 that includes side segments 134a, 134b and end segments 134c and 134d to form a generally rectangularly configured parametric seal for the outer edge 136 of the test panel 106. Dowels 135 on top 12 are directed into blind holes in seal plate 134 to locate it on the top 12. The dowels 135 also position panel 106 across opening 44.

More particularly, the seal plate 134 includes a groove 138 that extends continuously through the full perimeter of the seal plate 134 through its side walls as well as its end walls. Furthermore, the groove 138 is located vertically above the groove 124 and supportingly receives an O-ring seal 140 that engages the outer surface 118 of the panel 106 in line with the point of engagement between the O-ring seal 128 and the inner surface 116 of the panel 106 thereby to exert a clamping force therebetween. The pattern of the pores 112, 114 extends all the way to the outer edge 141 of the panel 106 and the opposed O-ring seals 128, 130 constitute a first seal barrier against leakage of air from the pressurizable space 66 outwardly along the support surface 120. The seal plate 134 has an undercut 142 along its inboard edge to accommodate the thickness of the test panel layers 108, 110 as best shown in FIG. 4. A seal surface 144 on the seal plate 134 extends to the outboard side on the undercut 142 completely around the full rectangular shape of the seal plate 134 and this seal surface 144 overlies the groove 126 with the O-ring seal 130 therein which presses against the seal surface 144 to define a second barrier against any flow leakage along the support surface 120 thereby to prevent small leakage of air through the pores which communicate with the perimeter of the test sheet. The O-ring seals 128, 130 and 140 are held in sealing engagement by a plurality of pressure applicators 146, each of which includes a base plate 148 fixedly secured by suitable means such as screws 150 to the cover 12 at spaced points therearound. The base 148 includes bifurcated arms 152, 154 thereon pivoted thereto by a pin 156. The bifurcated arms 152, 154 have a pin 158 directed therethrough secured to a two-sided clamp arm 160 with a threaded clamp screw 162 adjustably fixed on the end of clamp arm 160 by nuts 164, 166. A compression spring 168 is held between the nut 166 and a head 170 on the clamp screw 162 so that when the bifurcated arms 152, 154 are moved to the solid line position in FIG. 1, the arm 160 assumes an overtoggle position about pivot pin 172 through base 148 where compression spring 168 will produce a reaction through the head 170 against the upper surface of the seal plate at the point where the head 170 is in contact therewith to produce a solid downward pressure force against the seal plate 134 to assure that the O-ring seal components 128, 130, 140 will be positively compressed against the inner and outer surfaces 116, 118 of the test panel 106 to positively maintain the two pressure barriers against air leakage. It is important to provide such a positive seal to assure an extremely accurate measurement at very low flow rates through the porous metal of the test panel since even the smallest leaks can represent a significant source of error under low flow rates which are produced when a low pressure differential is present during the test operation.

A second embodiment of the present invention is illustrated at FIG. 5. It includes a channel-shaped resilient seal element 174 that engages the outer edge 176 and top and bottom surfaces 178, 180 of a test panel 182 of a fragment which is shown in FIG. 5. The resilient seal channel 174 is pressed together against the outer periphery of the test panel 182 by a seal plate 184 which has a hydraulic force 186 directed against the outer surface thereof to positively seal the resilient seal channel 174 against the upper surface 185 of a top 187 corresponding to the top 12 of a flow bench in FIGS. 1-4. In this arrangement, the test pressure maintained in a pressurizable space 188 corresponds to the pressurizable space 66 in the flow bench 10.

Another aspect of the invention in part is due to the fact that laminated porous metal for use in cooling gas turbine engine components can have a planar extent that bows or buckles when pressure is applied thereto. The result is a cantilever load effect operative at sealed perimeters of the panels 106, 182. Accordingly, in the present invention the seal plate 134 includes a pair of cross bars 189, 190 that are secured at their opposite ends to the seal plate at the segments 134c and 134d. Additionally, the bars 189, 190 are further reinforced by a plurality of transverse bars 192 with their opposite ends connected respectively to the seal plate segments 134a, 134b. The bars 192 are located below the cross bars 189, 190 and serve as a locater for a plurality of dependent pins 194, each of which includes a soft resilient tip 196 thereon engageable with the outer surface 118 of the test panel 106 as best seen in FIG. 3 to support the panel 106 at a plurality of spaced points throughout the middle third thereof along the lengths thereof to prevent buckling between the outer perimeter of the test panel 106 and the seals associated therewith thereby to prevent the seal being broken and a resultant small leakage of air flow from the pressurizable spaces 66 or 188 thereby to maintain a positive pressure differential and an accurately established flow rate across the test panel when it is clamped in place on the top 12 or the top 126.

In the case of the hydraulic force 124, the most preferable technique would be to use a hydraulic or pneumatic press which is illustrated by a platen 198 located against the outer surface of the seal plate 184 to apply a continuous pressure around the periphery of the seal plate 184 to maintain seal integrity during the test operation.

While the embodiments of the present invention, as herein disclosed, constitute a preferred form, it is to be understood that other forms might be adopted.

The embodiments of the invention in which an exclusive property or privilege is claimed are defined as follows:

1. An air flow test apparatus for determining the rate of air flow across a porous laminated metal panel of controlled porosity established by pores of controlled size extending through the lamina and distributed over the area of the lamina comprising: a top, a sealed box secured to said top, said box having an internal cavity and an upward facing opening therein, means for locating said panel in said top, seal means fixedly securing the panel to the top to cover the opening while simultaneously sealing the top, bottom and edge of the panel, means for supplying air pressure at spaced points therein into said box for producing a controlled uniform pressure differential across the sheet throughout its planar extent, and means for preventing the porous panel buckling upon application of air pressure to the box.

2. An air flow test apparatus for determining the rate of air flow across a porous laminated metal panel of controlled porosity established by pores of controlled size extending through the lamina and distributed over the area of the lamina comprising: a top, a sealed box secured to said top, said box having an internal cavity and an upward facing opening therein, means for locating said panel in said top, seal means fixedly securing the panel to the top to cover the opening while simultaneously sealing the top, bottom and edge of the panel, means for supplying air pressure at spaced points into said box for producing a controlled uniform pressure differential across the sheet throughout its planar extent, and means for preventing the porous panel buckling upon application of air pressure to the box, a screen member within said box cavity for minimizing air current eddies within said cavity to maintain uniform pressure conditions within said cavity during dynamic fluid flow from said cavity through the pores of said panel to atmosphere, and means for sampling and averaging pressure at spaced points within said cavity to determine the pressure differential across said sheet and the mass fluid flow across said sheet thereby to determine the effective flow area through said pores.

* * * * *